US008222387B2

(12) United States Patent
Lopato et al.

(10) Patent No.: US 8,222,387 B2
(45) Date of Patent: Jul. 17, 2012

(54) TRANSCRIPTION REGULATORS FOR REPRODUCTION ASSOCIATED PLANT PART TISSUE SPECIFIC EXPRESSION

(75) Inventors: Sergiy Lopato, Morphett Vale (AU); Ming Li, Xi'an (CN)

(73) Assignees: Grains Research & Development Corporation, Kingston (AU); Adelaide Research & Innovation Pty Ltd, Adelaide (AU)

( * ) Notice: Subject to any disclaimer, the term of this patent is extended or adjusted under 35 U.S.C. 154(b) by 595 days.

(21) Appl. No.: 12/302,779

(22) PCT Filed: May 31, 2007

(86) PCT No.: PCT/AU2007/000759
§ 371 (c)(1),
(2), (4) Date: Apr. 2, 2009

(87) PCT Pub. No.: WO2007/137361
PCT Pub. Date: Dec. 6, 2007

(65) Prior Publication Data
US 2009/0205074 A1    Aug. 13, 2009

(30) Foreign Application Priority Data

May 31, 2006   (AU) ................................ 2006902928

(51) Int. Cl.
*C12N 15/63*   (2006.01)
*C12N 15/82*   (2006.01)
*C12N 15/09*   (2006.01)
*C12N 15/00*   (2006.01)
*A01H 5/00*    (2006.01)

(52) U.S. Cl. ...... 536/24.1; 536/23.1; 800/287; 800/295; 800/278; 435/320.1; 435/468

(58) Field of Classification Search ........................ None
See application file for complete search history.

(56) References Cited

U.S. PATENT DOCUMENTS

| 7,214,786 | B2 | 5/2007 | Kovalic et al. |
| 7,365,185 | B2 * | 4/2008 | Boukharov et al. ......... 536/24.1 |
| 2004/0034888 | A1 | 2/2004 | Liu et al. |
| 2004/0214272 | A1 | 10/2004 | La Rosa et al. |
| 2007/0020621 | A1 | 1/2007 | Boukharov et al. |
| 2007/0039076 | A1 | 2/2007 | Boukharov et al. |

OTHER PUBLICATIONS

Bacic, Antony et al.; "Cellulose synthase (CESA) and cellulose-synthase-like (CSL) gene families of barley"; 2004 *Abstracts of Papers of the American Chemical Society*, vol. 227, No. 1, pp. U292.
Burton, Rachel A. et al.; "The CesA gene family of barley. Quantitative analysis of transcripts reveals two groups of co-expressed genes"; 2004, *Plant Physiology*, vol. 134, No. 1, pp. 224-236.
Burton, Rachel A. et al.; "The genetics and transcriptional profiles of the cellulose synthase-like HvCslf gene family in barley"; 2008, *Plant Physiology*, vol. 146, No. 4, pp. 1821-1833.
Carpita, Nicholas C.; "Structure and biogenesis of the cell walls of grasses"; 1996, *Annual Review of Plant Physiology and Plant Molecular Biology Annual Reviews*, pp. 445-476.
Han, F. et al.; "Mapping of beta-glucan content and beta-glucanase activity loci in barley grain and malt"; 1995, *Theoretical and Applied Genetics*, vol. 91, No. 6-7, pp. 921-927.
Hazen, S.P. et al.; "Cellulose Synthase-Like Genes of Rice"; 2002, *Plant Physiology*, vol. 128, pp. 336-340.
Hunter, Charles T. et al.; "Analysis of Mu-induced knockout mutations in cell wall biosynthetic genes of maize identified through reverse genetics"; 2005, *Plant Biology*, vol. 2005, pp. 177.
Mayer, R. et al.; "Polypeptide Composition of Bacterial Cyclic Diguanylic Acid-Dependent Cellulose Synthase and the Occurrence of Immunologically Crossreacting Proteins in Higher Plants"; 1991, *Proceedings of the National Academy of Sciences*, vol. 88, No. 12, pp. 5472-5476.
Medhurst, A. et al.; "Towards determining a role in cell wall synthesis for the cellulose synthase-like D and F genes of barley"; 2005, *Comparative Biochemistry and Physiology Part A Molecular & Integrative Physiology*, vol. 141, No. 3, Suppl. S., pp. S265-S266.
Richmond, Todd A. et al.; "Integrative approaches to determining Csl function"; 2001, *Plant Molecular Biology*, vol. 47, No. 1-2, pp. 131-143.
Database EMBL, 2001, "*Oryza sativa* CSLF6 mRNA, partial cds"; EBI Accession No. EMBL:AF435645, 4 pages.
Katagiri, S., et al., "End Sequencing and Chromosomal in silico Mapping of BAC Clones Derived from an *indicia* Rice Cultivar, Kasalath," *Breeding Science*, vol. 54, pp. 273-279 (2004).
Yu, J., et al., "The Genomes of *Oryza sativa*: A History of Duplications," *PLoS Biology*, vol. 3(2), pp. 266-281 (Feb. 2005).
GenBank Accession No. CA760707, Bennett, J., et al., "BR060007A20D07.ab1 IRRI clones *Oryza sativa* (indica cultivar group) cDNA clone BR060007A20D07.ab1 similar to no homology, mRNA," 2 pgs. (Nov. 27, 2002).
GenBank Accession No. CL757424, Kim, H., et al., "OR_BBa0125N15.r OR_BBa *Oryza nivara* genomic clone OR_BBa0125N15 3', genomic survey sequence," 2 pgs (Jul. 27, 2004).
GenBank Accession No. CL981933, Ma, L., et al., "OsIFSC046394 *Oryza sativa* express library *Oryza sativa* (indica cultivar-group) genomic, genomic survey sequence," 2 pgs. (Sep. 21, 2004).
GenBank Accession No. CW759605, Kim H., et al., "OG_BBa0067N19.f OG_BBa *Oryza glaberrima* genomic clone OG_BBa0067N19 5', genomic sequence survey," 2 pgs. (Nov. 9, 2004).

(Continued)

*Primary Examiner* — Brent T Page
(74) *Attorney, Agent, or Firm* — Kilpatrick Townsend & Stockton LLP

(57) ABSTRACT

The present invention relates generally to transcriptional control sequences for effecting expression of a nucleotide sequence of interest in a plant. The present invention is predicated, in part, on the identification and functional characterization of transcriptional control sequences derived from genes which encode polypeptides comprising the amino acid sequence set forth in SEQ ID NO: 1 and homologs thereof. Among other things, the present invention has identified that transcriptional control sequences derived from the subject genes can effect specific or preferential expression of an operably connected nucleotide sequence in a reproduction-associated plant part such as a seed or anther.

11 Claims, 8 Drawing Sheets

OTHER PUBLICATIONS

GenBank Accession No. AG855519, Katagiri, S., et al., "*Oryza sativa* (indica cultivar-group) genomic DNA, BAC end sequence, BAC clone:K0150F06_F, genomic survey sequence," 2 pgs. (Nov. 3, 2004).

GenBank Accession No. CZ832828, Kim, H., et al., "OC_Ba0215c19.r OC_Ba *Oryza coarctata* genomic clone OC_Ba0215c19 3', genomic survey sequence," 2 pgs. (Jul. 26, 2005).

* cited by examiner

FIGURE 2

```
                        1                                                50
OsPR9a_CA760707   (1)   MAMRRMNNPLTAVFLAMVMASTLP--S--CYAANGTCYDNMFCRGNVC
         WENDL9   (1)   MAPMSNNTRKAVVFLLMVMASTLSSSSCYARTINGANPPNYCFYVNKC
      Consensus   (1)   MA    A   VFL LMVMASTL  S      DDG   L      D  C 51                          88
OsPR9a_CA760707  (47)   KLRCRYLG---NPDNAPCYCKSKPDGSAQCCCQRSSL-
         WENDL9  (51)   KERCQIACSLSNKPSTGPYCKHN-----QCCCA-----
      Consensus  (51)   K RC        F     YCK       QCCC
```

FIGURE 3

```
   1    GTTCTTCAGG GACGAAAATG ATACTCCGTA GAATAGTAAC CTCGAACAAT
  51    TTGTAGTATT TATGTTCGAA ACAGATTTAG AATTTGTTTT GTTTGAAGTT
 101    GCAAACATAA TATTCAGAGA GCCGCATCAA AATTCCATAA ATTAAATTCA
 151    GTATACCCGG CACACTTTGT CGTTCCTTGG TGCAATTTGA AAACAAGGGG
 201    TTTGGAGCAT CGGTTGCTAT AGGCCTATAG CCTTGCCGGC GAAAATAAGA
 251    TGACTAATTA CTCAATGATT TGTACTCAAA TGATCGACCA GGAATTGAAG
 301    GTAGCAATGT AGCATTCATA TTGCAAAATC TGTAGTACAT TATATTGAAT
 351    TGTTTCTTAC AAAGAATACA TATAGCCAGA AGGGCTGCCT ATTTCCAGTT
 401    AGTAAAGTAG GGGAGTGTTA ACCTATATTG AATCTGGAAA TAGGAAGAAA
 451    ACCTCATGTG CTTAAAAAAA ATATAGGCCT CATTTAGAAT GTAACTTGCC
 501    TACGTTTCTC TTAACACCAT GAATGTGTTT TTATTGGAAA AGTTATAGTC
 551    GAGGCAACTT AGAATTAAGC ATCGGAGCAT GTATTTTTAT GGTATAAGCT
 601    TTCAGAAGGT GTTCTTGCAT ACATGAAAAG AAGAAAAGGA AAGAAAAAAC
 651    ATTGAACTAA TTGTAAGTGT AGAAGTTGTG TTGCATTACC TATTTACCTT
 701    TACTATGTTG AAAGTGTAAC AAAATATGTG CATCTAATAT ATGAATGTGT
 751    GAAACTTGAC ACTATCAATG AATTCTCAAG TGTTGAAATC CAGGAGATTT
 801    GTATGGTAGA CCTATCGGAT CCACCAATCA GATATACTCC ATCTAACACC
 851    CATAAATACA ATTGAAATA CACGTCAACA TTAATGCATG AAAAATCATA
 901    AATGCAATGA GTGTCTAAGA TCCTACCGTG CCTCTCTCTA TATAAACTCC
 951    TCTAACATAT ACAATAGAGT CCATATCGAA GTAATATTCT TCTAATATGT
1001    CCAATTGTCC ACCATGAATA GAAGGATGGG TTACTCATAG GCTGTTGTTT
1051    TCATGTCTTC CACCTTGCCA TCTGCTCTCT AAGACGTTAA CTTTCACTAA
1101    ACTGCAATTT TAACTTTTTG TTTATTAACC TTTGTTTGAT ATGTGTTCAA
1151    TAATCTATTT CAGTTTTGGA TCATTTTTCG AATTTGACAA AATTACATGC
1201    TACAAAGTTG AGTTCTACTA AGGGAATATG TATAAGCTTA CATGCACATC
1251    CTGTGGTTTC CCTCGCTCTC CGTACTACTG CAGGACTAAA CCAAATGGTT
1301    CATCACAATG TTGTTGTGAA CGATACTTCT TCGGTGATAT CAGAATGACA
1351    TTAGAAGCGA TCAATTGGTG GCCTTCTTGC TTGGTCAATA TTGAAAAAAA
1401    AAATGATGTT CAGGATTGAA TGTAATAGTC TAATACTATT AGATTCCATG
1451    AATGTGTACA ACAATATAAT AATCAATAAA TTCTCAAATC TTGAAATCTA
1501    CAATAAATGC AAATAGGGAT ATGTACAATA AATCTAACCA TCTAGGAATC
1551    CTCCAAAACC ATATACTTTG TGCTATCTAA CACAATTAAT GCAACTGCAA
1601    ATATATATCA ACATCAATGC AGGGAAAAAC ATAAATACAT TGAATGCCTA
1651    AGGTCTATTG TGCCTCTATA CAAACTCCTG CAAAGCTCTA ACATATAAAG
                                                M   A   M   R   M   G  ·
1701    TAGATAAGAT TGTGTTATAA ATCATCTAAT ATGGCCATGA GAAGGATGGG
         · N   P   L   T   A   V   F   L   A   V   M   V   M   S   S   T   L ·
1751    GAACCCATTG ACTGCTGTTT TCTTGGCTGT TATGGTCATG TCCTCCACCC
         · P   S   C   Y   A
1801    TACCATCTTG CTATGCAGGT ACTAGGGATA TATGCTCTCT AAGACTTTTT
1851    AACTTTCACA TCACTACACT TTAACTTTTC ATGTATTAAT CTTTGTTTCG
1901    ATGTGTGTTC AATAATCAAA TGTTGGCTTT GAATCATTTC ATCGTGAAAC
                    D   E   G   T   C   Y   D   V   M   F   C   R   G   D
1951    GTGAAGCCGA TGAAGGGACG TGCTACGATG TCATGTTCTG CCGGGGTGAT
         V   C   K   L   R   C   R   Y   L   G   Y   P   D   N   A   P   C ·
2001    GTGTGCAAGC TTAGATGCAG ATACCTTGGT TACCCTGACA ATGCTCCGTG
         · Y   C   K   S   K   P   D   G   S   A   Q   C   C   C   E   R   S ·
2051    CTACTGCAAG AGTAAACCGG ATGGTTCGGC ACAATGCTGC TGCGAACGAT
         · S   L   *
2101    CATCACTCTG ATATCGGAAT GGAACCAGTG ATTAATGGTG GCTTTCTTGT
2151    TTGGTCAATG CTATATATGA TTCATGATTA ATGTAGAAGC CATTGATCCC
2201    TACTTGCTCT TGCATATGTA AATTGGCGAT CGAACAAGTA TTTTCAGGTC
2251    TCATGCATAC TCAATAAACT TGGATTTGCT ATTTGTTACT ACTTCACTGA
```

WT 1 2 3 4 5 6 7 8 9

SEQUENCE LISTING

<160> NUMBER OF SEQ ID NOS: 11

<210> SEQ ID NO 1
<211> LENGTH: 80
<212> TYPE: PRT
<213> ORGANISM: Oryza sativa

<400> SEQUENCE: 1

```
Met Ala Met Arg Arg Met Gly Asn Pro Leu Thr Ala Val Phe Leu Ala
1               5                   10                  15

Val Met Val Met Ser Ser Thr Leu Pro Ser Cys Tyr Ala Ala Asp Glu
            20                  25                  30

Gly Thr Cys Tyr Asp Val Met Phe Cys Arg Gly Asp Val Cys Lys Leu
        35                  40                  45

Arg Cys Arg Tyr Leu Gly Tyr Pro Asp Asn Ala Pro Cys Tyr Cys Lys
    50                  55                  60

Ser Lys Pro Asp Gly Ser Ala Gln Cys Cys Gln Arg Ser Ser Leu
65                  70                  75                  80
```

<210> SEQ ID NO 2
<211> LENGTH: 471
<212> TYPE: DNA
<213> ORGANISM: Oryza sativa

<400> SEQUENCE: 2

```
taggtgagag gacgagacaa ggggaaagca gattgtgtta tagatcatct aatatggcca      60
tgagaaggat ggggaaccca ttgactgctg ttttcttggc tgttatggtc atgtcttcca     120
```

```
ccctaccatc ttgctatgca gccgatgaag ggacgtgcta cgacgtcatg ttctgccggg      180
gtgacgtgtg caagcttaga tgcagatacc ttggttaccc tgacaatgct ccgtgctatt      240
gcaagagtaa accagatggt tcggcacagt gctgctgcca acgatcatca ctatgatatt      300
ggaatggaac cagtgattaa tggtggcttt cttgtttgat caatgctata tatgattcat      360
gattaatgta gtagccattg atccctactt gctcttgcat atgtaaattg gcgatcaaac      420
aagtattttc aggtctcatg catactcaat aaactcatga tttctctcaa a              471
```

```
<210> SEQ ID NO 3
<211> LENGTH: 1730
<212> TYPE: DNA
<213> ORGANISM: Oryza sativa

<400> SEQUENCE: 3
```

```
gttcttcagg gacgaaaatg atactccgta gaatagtaac ctcgaacaat ttgtagtatt       60
tatgttcgaa acagatttag aatttgtttt gtttgaagtt gcaaacataa tattcagaga      120
gccgcatcaa aattccataa attaaattca gtatacccgg cacactttgt cgttccttgg      180
tgcaatttga aaacaagggg tttggagcat cggttgctat aggcctatag ccttgccggc      240
gaaaataaga tgactaatta ctcaatgatt tgtactcaaa tgatcgacca ggaattgaag      300
gtagcaatgt agcattcata ttgcaaaatc tgtagtacat tatattgaat gtttcttac      360 aaagaataca tatagccaga agggctgcct atttccagtt agtaaagtag gggagtgtta      420
acctatattg aatctggaaa taggaagaaa acctcatgtg cttaaaaaaa ataggcct       480 catttagaat gtaacttgcc tacgtttctc ttaacaccat gaatgtgttt ttattggaaa      540
agttatagtc gaggcaactt agaattaagc atcggagcta gtattttat ggtataagct      600 ttcagaaggt gttcttgcat acatgaaaag aagaaaagga agaaaaaac attgaactaa      660 ttgtaagtgt agaagttgtg ttgcattacc tatttacctt tactatgttg aaagtgtaac      720
aaaatatgtg catctaatat atgaatgtgt gaaacttgac actatcaatg aattctcaag      780
tgttgaaatc caggagattt gtatggtaga cctatcggat ccaccaatca gatatactcc      840
atctaacacc cataaataca attgaaaata cacgtcaaca ttaatgcatg aaaaatcata      900
aatgcaatga gtgtctaaga tcctaccgtg cctctctcta tataaactcc tctaacatat      960
acaatagagt ccatatcgaa gtaatattct tctaatatgt ccaattgtcc accatgaata     1020
gaaggatggg ttactcatag gctgttgttt tcatgtcttc caccttgcca tctgctctct     1080
aagacgttaa ctttcactaa actgcaattt taacttttg tttattaacc tttgtttgat      1140
atgtgttcaa taatctatttt cagttttgga tcattttcg aatttgacaa aattacatgc     1200
tacaaagttg agttctacta agggaatatg tataagctta catgcacatc ctgtggtttc     1260
cctcgctctc cgtactactg caggactaaa ccaaatggtt catcacaatg ttgttgtgaa     1320
cgatacttct tcggtgatat cagaatgaca ttagaagcga tcaattggtg gccttcttgc     1380
ttggtcaata ttgaaaaaaa aaatgatgtt caggattgaa tgtaatagtc taatactatt     1440
agattccatg aatgtgtaca acaatataat aatcaataaa ttctcaaatc ttgaaatcta     1500
caataaatgc aaataggat atgtacaata aatctaacca tctaggaatc ctccaaaacc     1560
atatactttg tgctatctaa cacaattaat gcaactgcaa atatatatca acatcaatgc     1620
agggaaaaac ataaatacat tgaatgccta aggtctattg tgcctctata caaactcctg     1680
caaagctcta acatataaag tagataagat tgtgttataa atcatctaat                1730
```

<210> SEQ ID NO 4
<211> LENGTH: 549
<212> TYPE: DNA
<213> ORGANISM: Oryza sativa

<400> SEQUENCE: 4

```
tcatctaata tggccatgag aaggatgggg aacccattga ctgctgtttt cttggctgtt      60
atggtcatgt cctccaccct accatcttgc tatgcaggta ctagggatat atgctctcta     120
agacttttta actttcacat cactacactt taacttttca tgtattaatc tttgtttcga     180
tgtgtgttca ataatcaaat gttggctttg aatcatttca tcgtgaaacg tgaagccgat     240
gaagggacgt gctacgatgt catgttctgc cggggtgatg tgtgcaagct tagatgcaga     300
taccttggtt accctgacaa tgctccgtgc tactgcaaga gtaaaccgga tggttcggca     360
caatgctgct gcgaacgatc atcactctga tatcggaatg gaaccagtga ttaatggtgg     420
cttcttgtt tggtcaatgc tatatatgat tcatgattaa tgtagaagcc attgatccct      480
acttgctctt gcatatgtaa attggcgatc gaacaagtat tttcaggtct catgcatact     540
caataaact                                                             549
```

<210> SEQ ID NO 5
<211> LENGTH: 78
<212> TYPE: PRT
<213> ORGANISM: Triticum aestivum

<400> SEQUENCE: 5

```
Met Ala Pro Met Ser Asn Ala Thr Arg Lys Ala Val Val Phe Val Leu
1               5                  10                  15
Leu Met Val Met Ala Ser Thr Leu Ser Ser Ser Cys Tyr Ala Arg
            20                  25                  30
Thr Ile Glu Asp Gly Ala Asn Pro Pro Leu Tyr Cys Phe Tyr Val Glu
        35                  40                  45
Lys Cys Lys Glu Arg Cys Gln Ile Ala Cys Ser Leu Ser Phe Lys Pro
    50                  55                  60
Ser Thr Gly Pro Tyr Cys Lys His Asn Gln Cys Cys Ala
65                  70                  75
```

<210> SEQ ID NO 6
<211> LENGTH: 413
<212> TYPE: DNA
<213> ORGANISM: Triticum aestivum

<400> SEQUENCE: 6

```
acggcatcct taagcacaca acaaacaaag aagtgattcc ttgtcgatct cttggtcatg      60
gcacccatga gcaatgcgac caggaaggct gtggttttg tgcttcttat ggttatggct      120
tctaccctat catcatcgtc ttgctacgcc cgcacaattg aagatggagc caatcctcca     180
ttgtactgct tctatgtgga aaagtgcaaa gaacgttgcc agatcgcatg cagcctcagc     240
tttaagccct caactgggcc gtattgcaag cacaatcagt gttgttgtgc ctagaataat     300
gcttcttttt tttactaaat aaaggaataa ttttactaca tatgcttgca aatgtagtat     360
tggttactga ctaattatac aattgagcct cttgtgttgt ctggtccact aaa            413
```

<210> SEQ ID NO 7
<211> LENGTH: 21
<212> TYPE: DNA
<213> ORGANISM: Artificial
<220> FEATURE:
<223> OTHER INFORMATION: Oligonucleotide Primer -continued

```
<400> SEQUENCE: 7
gcacaatcag tgttgttgtg c                                         21

<210> SEQ ID NO 8
<211> LENGTH: 21
<212> TYPE: DNA
<213> ORGANISM: Artificial
<220> FEATURE:
<223> OTHER INFORMATION: Oligonucleotide Primer

<400> SEQUENCE: 8
gtggaccaga caacacaaga g                                         21

<210> SEQ ID NO 9
<211> LENGTH: 27
<212> TYPE: DNA
<213> ORGANISM: Artificial
<220> FEATURE:
<223> OTHER INFORMATION: Oligonucleotide Primer

<400> SEQUENCE: 9
gttcttcagg gacgaaaatg atactcc                                   27

<210> SEQ ID NO 10
<211> LENGTH: 31
<212> TYPE: DNA
<213> ORGANISM: Artificial
<220> FEATURE:
<223> OTHER INFORMATION: Oligonucleotide Primer

<400> SEQUENCE: 10
attagatgat ttataacaca atcttatcta c                              31

<210> SEQ ID NO 11
<211> LENGTH: 20
<212> TYPE: DNA
<213> ORGANISM: Artificial
<220> FEATURE:
<223> OTHER INFORMATION: Oligonucleotide Primer

<400> SEQUENCE: 11
actgaatgcc cacaggccgt                                           20
```

TRANSCRIPTION REGULATORS FOR REPRODUCTION ASSOCIATED PLANT PART TISSUE SPECIFIC EXPRESSION

FIELD OF THE INVENTION

The present invention relates generally to transcriptional control sequences for effecting expression of a nucleotide sequence of interest in a plant. More particularly, the present invention relates to transcriptional control sequences that direct specific or preferential expression of an operably connected nucleotide sequence of interest in a reproduction-associated plant part, such as a seed or anther.

BACKGROUND OF THE INVENTION

The primary emphasis in genetic modification has been directed to prokaryotes and mammalian cells. For a variety of reasons, plants have proven more intransigent than other eukaryotic cells to genetically manipulate. However, in many instances, it is desirable to effect transcription of an introduced nucleotide sequence of interest in a plant.

Expression of a heterologous DNA sequence in a plant is dependent, in part, upon the presence of an operably linked transcriptional control sequence, such as a promoter or enhancer, which is functional within the plant. The transcriptional control sequence determines when and where within the plant the heterologous DNA sequence is expressed. For example, where continuous expression is desired throughout the cells of a plant, constitutive promoters are utilized. In contrast, where gene expression in response to a stimulus is desired, an inducible promoter may be used. Where expression in specific tissues or organs is desired, a tissue-specific promoter may be used.

Accordingly, there is a substantial interest in identifying transcriptional control sequences, such as promoters or enhancers, which are active in plants.

Frequently, it is desirable to specifically or preferentially direct transcription in particular plant organs, tissues or cell types, or at particular developmental stages of the plant.

For example, the nutritional value of grain in cereal crop plants can be increased by genetic manipulation of the plant's genome with a seed-preferred promoter operably linked to a heterologous gene that encodes for the production of one or more nutrients. 'Golden Rice' provides a specific example of a plant with grain having an altered nutritional content (increased β-carotene) as a result of the grain-specific expression of a transgene (see Paine et al., *Nature Biotechnology* 23: 482-487, 2005).

Furthermore, expression of a toxic polypeptide (such as diphtheria toxin, barnase or the like) in male or female reproduction-associated plant parts of a plant may be used to effect male or female sterility in the plant.

Thus, isolation and characterization of transcriptional control sequences, which can serve as regulatory regions for the expression of heterologous nucleotide sequences of interest in reproduction-associated plant parts, such as seeds or anthers, would be desirable for use in the genetic manipulation of plants.

Reference to any prior art in this specification is not, and should not be taken as, an acknowledgment or any form of suggestion that this prior art forms part of the common general knowledge in any country.

SUMMARY OF THE INVENTION

The present invention is predicated, in part, on the identification and functional characterisation of transcriptional control sequences derived from plant genes which encode polypeptides comprising the amino acid sequence set forth in SEQ ID NO: 1 and homologs thereof. Among other things, the present invention has identified that transcriptional control sequences derived from the subject plant genes can effect specific or preferential expression of an operably connected nucleotide sequence in a reproduction-associated plant part.

Accordingly, in a first aspect, the present invention provides a method for effecting specific or preferential expression of a nucleotide sequence of interest in a reproduction-associated plant part, the method comprising effecting transcription of the nucleotide sequence of interest in a plant under the transcriptional control of:

a transcriptional control sequence derived from a gene which encodes a polypeptide comprising the amino acid sequence set forth in SEQ ID NO: 1 or a homolog thereof; or a functionally active fragment or variant of said transcriptional control sequence;

wherein the nucleotide sequence of interest is heterologous with respect to the transcriptional control sequence or the functionally active fragment of variant thereof.

In some embodiments, the reproduction-associated plant part comprises a plant seed. In further embodiments, the reproduction-associated plant part comprises an anther.

In a second aspect, the present invention provides a nucleic acid construct comprising a nucleotide sequence selected from the list consisting of:

a nucleotide sequence defining a transcriptional control sequence derived from a gene which encodes a polypeptide comprising the amino acid sequence set forth in SEQ ID NO: 1 or a homolog thereof; and a nucleotide sequence defining a functionally active fragment or variant of said transcriptional control sequence.

In a third aspect, the present invention provides a cell comprising a nucleic acid construct of the second aspect of the invention or a genomically integrated form thereof.

In a fourth aspect, the present invention contemplates a multicellular structure comprising one or more cells of the third aspect of the invention. In one embodiment, the multicellular structure comprises a plant or a part, organ or tissue thereof.

In a fifth aspect, the present invention provides an isolated nucleic acid molecule comprising a nucleotide sequence defining:

a transcriptional control sequence derived from a gene which encodes a polypeptide comprising the amino acid sequence set forth in SEQ ID NO: 1 or a homolog thereof; or a functionally active fragment or variant of said transcriptional control sequence.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to herein by a sequence identifier number (SEQ ID NO:). A summary of the sequence identifiers is provided in Table 1. A sequence listing is provided at the end of the specification.

TABLE 1

Summary of Sequence Identifiers

| Sequence Identifier | Sequence | Identifier in sequence listing |
|---|---|---|
| SEQ ID NO: 1 | OsWENDL9L amino acid sequence | 400 <1> |
| SEQ ID NO: 2 | OsWENDL9L cDNA nucleotide sequence | 400 <2> |
| SEQ ID NO: 3 | OsPR9a promoter nucleotide sequence | 400 <3> |
| SEQ ID NO: 4 | OsWENDL9L genomic nucleotide sequence | 400 <4> |
| SEQ ID NO: 5 | Wheat WENDL9 amino acid sequence | 400 <5> |
| SEQ ID NO: 6 | Wheat WENDL9 cDNA nucleotide sequence | 400 <6> |
| SEQ ID NO: 7 | QPCRf primer | 400 <7> |
| SEQ ID NO: 8 | QPCRr primer | 400 <8> |
| SEQ ID NO: 9 | C_PR9a primer | 400 <9> |
| SEQ ID NO: 10 | PR9r primer | 400 <10> |
| SEQ ID NO: 11 | GUS5'rev primer | 400 <11> |

DESCRIPTION OF EXEMPLARY EMBODIMENTS

It is to be understood that the following description is for the purpose of describing particular embodiments only and is not intended to be limiting with respect to the above description.

The present invention is predicated, in part, on the identification and functional characterisation of transcriptional control sequences derived from plant genes which encode polypeptides comprising the amino acid sequence set forth in SEQ ID NO: 1, or homologs thereof.

As used herein, the term "transcriptional control sequence" should be understood as a nucleotide sequence that modulates at least the transcription of an operably connected nucleotide sequence. As such, the transcriptional control sequences of the present invention may comprise any one or more of, for example, a leader, promoter, enhancer or upstream activating sequence.

Generally, the term "transcriptional control sequence" as used herein at least includes a promoters A "promoter" as referred to herein, encompasses any nucleic acid that confers, activates or enhances expression of an operably connected nucleotide sequence in a cell.

As used herein, the term "operably connected" refers to the connection of a transcriptional control sequence, such as a promoter, and a nucleotide sequence of interest in such a way as to bring the nucleotide sequence of interest under the transcriptional control of the transcriptional control sequence. For example, promoters are generally positioned 5' (upstream) of a nucleotide sequence to be operably connected to the promoters. In the construction of heterologous transcriptional control sequence/nucleotide sequence of interest combinations, the promoter is generally positioned at a distance from the transcription start site that is approximately the same as the distance between that promoter and the gene it controls in its natural setting, ie. the gene from which the promoter is derived. However, as is known in the art, some variation in this distance can be accommodated without loss of promoter function.

The present invention contemplates transcriptional control sequences which are derived from a gene which either encodes either a polypeptide comprising the amino acid sequence set forth in SEQ ID NO: 1 or encodes a homolog of this polypeptide. The term "derived from", as it is used herein, refers to a source or origin for the transcriptional control sequence. For example, a transcriptional control sequence "derived from a gene which encodes a polypeptide comprising the amino acid sequence set forth in SEQ ID NO: 1" refers to a transcriptional control sequence which, in its native state, exerts at least some transcriptional control over a gene which encodes a polypeptide comprising the amino acid sequence set forth in SEQ ID NO: 1 in an organism, such as a plant.

Among other things, the present invention has identified that transcriptional control sequences that are derived from genes which encode polypeptides comprising the amino acid sequence set forth in SEQ ID NO: 1, or homologs thereof, can effect specific or preferential expression of an operably connected nucleotide sequence in a reproduction-associated plant part.

Accordingly, in a first aspect, the present invention provides a method for effecting specific or preferential expression of a nucleotide sequence of interest in a reproduction-associated plant part, the method comprising effecting transcription of the nucleotide sequence of interest in a plant under the transcriptional control of:

a transcriptional control sequence derived from a gene which encodes a polypeptide comprising the amino acid sequence set forth in SEQ ID NO: 1 or a homolog thereof; or a functionally active fragment or variant of said transcriptional control sequence;

wherein the nucleotide sequence of interest is heterologous with respect to the transcriptional control sequence or the functionally active fragment of variant thereof.

The term "homolog", as used herein with reference to homologs of polypeptides comprising the amino acid sequence set forth in SEQ ID NO: 1, is used herein in its broadest sense. Therefore, the term "homolog" should be understood to include, for example, homologs, orthologs, paralogs, mutants and variants of polypeptides comprising the amino acid sequence set forth in SEQ ID NO: 1.

In some embodiments, the homolog, ortholog, paralog, mutant or variant of a polypeptide comprising the amino acid sequence set forth in SEQ ID NO: 1 comprises an amino acid sequence which comprises at least 35% sequence identity, at least 50% sequence identity, at least 65% sequence identity, at least 80% sequence identity, at least 90% sequence identity or at least 95% sequence identity to the amino acid sequence set forth in SEQ ID NO: 1.

When comparing amino acid sequences to calculate a percentage identity, the compared sequences should be compared over a comparison window of at least 20 amino acid residues, at least 40 amino acid residues, at least 60 amino acid residues or over the full length of SEQ ID NO: 1. The comparison window may comprise additions or deletions (ie. gaps) of about 20% or less as compared to the reference sequence (which does not comprise additions or deletions) for optimal alignment of the two sequences. Optimal alignment of sequences for aligning a comparison window may be conducted by computerized implementations of algorithms such the BLAST family of programs as, for example, disclosed by Altschul et al. (*Nucl. Acids Res.* 25: 3389-3402, 1997). A detailed discussion of sequence analysis can be found in Unit 19.3 of Ausubel et al. ("Current Protocols in Molecular Biology" John Wiley & Sons Inc, 1994-1998, Chapter 15, 1998).

Exemplary homologs of the polypeptide comprising the amino acid sequence set forth in SEQ ID NO: 1 include a polypeptide comprising the amino acid sequence set forth in SEQ ID NO: 5.

As such, some embodiments of the invention, the transcriptional control sequences contemplated herein are derived from a gene which encodes a polypeptide comprising the amino acid sequence set forth in SEQ ID NO: 1, SEQ ID NO: 5 or a homolog of either of the foregoing amino acid sequences.

The present invention contemplates the use of transcriptional control sequences derived from any organism. However, in some embodiments of the present invention, the transcriptional control sequences contemplated herein are derived from plants.

The term "plant" should be understood to include monocotyledonous angiosperm plants, dicotyledonous angiosperm plants and gymnosperm plants. The term "plant" should also be understood to specifically include a cereal crop plant.

As used herein, the term "cereal crop plant" may be a member of the Poaceae (grass family) that produces grain. Examples of Poaceae cereal crop plants include wheat, rice, maize, millets, sorghum, rye, triticale, oats, barley, teff, wild rice, spelt and the like. The term cereal crop plant should also be understood to include a number of non-Poaceae plant species that also produce edible grain and are known as the pseudocereals, such as amaranth, buckwheat and quinoa.

In one specific embodiment, the transcriptional control sequence is derived from rice (*Oryza sativa*).

In another specific embodiment, the transcriptional control sequence is derived from a gene which comprises an open reading frame comprising the nucleotide sequence set forth in SEQ ID NO: 2.

In yet another specific embodiment, the transcriptional control sequence comprises the nucleotide sequence set forth in SEQ ID NO: 3 or a functionally active fragment or variant thereof.

As set out above, the present invention also contemplates functionally active fragments or variants of a transcriptional control sequence. As referred to herein, a "functionally active fragment or variant" refers to a fragment or variant which retains the functional activity of a transcriptional control sequence.

"Functionally active fragments", as contemplated herein, may be of any length wherein the fragment is capable of effecting transcriptional control of an operably connected nucleotide sequence. In some embodiments, the functionally active fragment is capable of specifically or preferentially directing the expression of an operably connected nucleotide sequence in a reproduction-associated plant part.

Generally, a "fragment" may be at least 100 nucleotides (nt), at least 500 nt, still or at least 1000 nt in length. In some embodiments of the invention the fragment may comprise at least 100 nt, at least 500 nt or at least 1000 nt contiguous bases from the nucleotide sequence set forth in SEQ ID NO: 3.

"Functionally active variants" of the transcriptional control sequence of the invention include orthologs, mutants, synthetic variants, analogs and the like which are capable of effecting transcriptional control of an operably connected nucleotide sequence. In some embodiments, the functionally active variant is capable of specifically or preferentially directing the expression of an operably connected nucleotide sequence in a reproduction-associated plant part.

For example, the term "variant" should be considered to specifically include, for example, orthologous transcriptional control sequences from other organisms; mutants of the transcriptional control sequence; variants of the transcriptional control sequence wherein one or more of the nucleotides within the sequence has been substituted, added or deleted; and analogs that contain one or more modified bases or DNA or RNA backbones modified for stability or for other reasons.

"Modified" bases include, for example, tritylated bases and unusual bases such as inosine.

In some embodiments, the functionally active fragment or variant comprises at least 50% sequence identity, at least 65% sequence identity, at least 80% sequence identity, at least 90% sequence identity or at least 95% sequence identity to the nucleotide sequence set forth in SEQ ID NO: 3.

When comparing nucleic acid sequences to calculate a percentage identity, the compared nucleotide sequences should be compared over a comparison window of at least 100 nucleotide residues, at least 200 nucleotide residues, at least 500 nucleotide residues, at least 1000 nucleotide residues or over the full length of SEQ ID NO: 3. The comparison window may comprise additions or deletions (ie. gaps) of about 20% or less as compared to the reference sequence (which does not comprise additions or deletions) for optimal alignment of the two sequences. Optimal alignment of sequences for aligning a comparison window may be conducted by computerized implementations of algorithms such the BLAST family of programs as, for example, disclosed by Altschul et al. (1997, supra). A detailed discussion of sequence analysis can be found in Unit 19.3 of Ausubel et al. (1998, supra).

In further embodiments, the functionally active fragment or variant may comprise a nucleic acid molecule which hybridises to a nucleic acid molecule defining a transcriptional control sequence of the present invention under stringent conditions. In some specific embodiments, the functionally active fragment or variant comprises a nucleic acid molecule which hybridises to a nucleic acid molecule comprising the nucleotide sequence set forth in SEQ ID NO: 3 under stringent conditions.

As used herein, "stringent" hybridisation conditions will be those in which the salt concentration is less than about 1.5 M Na ion, typically about 0.01 to 1.0 M Na ion concentration (or other salts) at pH 7.0 to 8.3 and the temperature is at least 30° C. Stringent conditions may also be achieved with the addition of destabilizing agents such as formamide. Stringent hybridisation conditions may be low stringency conditions, medium stringency conditions or high stringency conditions. Exemplary low stringency conditions include hybridisation with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridisation in 40 to 45% formamide, 1.0 M NaCl, 1% SDS at 37° C., and a wash in 0.5× to 1×SSC at 55 to 60° C. Exemplary high stringency conditions include hybridisation in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity of hybridisation is also a function of post-hybridization washes, the critical factors of which are the ionic strength and temperature of the final wash solution. For DNA-DNA hybrids, the $T_m$ can be approximated from the equation of Meinkoth and Wahl (*Anal. Biochem.* 138: 267-284, 1984), ie. $T_m = 81.5°$ C. $+16.6$ (log M) $+0.41$ (% GC) $-0.61$ (% form) $-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of different degrees of complementarity. For example, sequences with ≥90% identity can be hybridised by decreasing the $T_m$ by about 10° C. Generally, stringent conditions are selected to be about 5° C. lower than the thermal melting point ($T_m$) for the specific sequence and its complement at a defined ionic strength and pH. However, high stringency conditions can utilize a hybridization and/or wash at, for example, 1, 2, 3, or 4° C. lower than the thermal melting point ($T_m$); medium stringency conditions can utilize a hybridization and/or wash at, for example, 6, 7, 8, 9, or 10° C. lower than the thermal melting point ($T_m$); low stringency conditions can utilize a hybridization and/or wash at, for example, 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), the SSC concentration may be increased so that a higher temperature can be used. An extensive guide to the hybridization of nucleic acids is found in Tijssen (*Laboratory Techniques in Biochemistry and Molecular Biology-Hybridization with Nucleic Acid Probes*, Pt I, Chapter 2, Elsevier, N.Y., 1993), Ausubel et al., eds. (*Current Protocols in Molecular Biology*, Chapter 2, Greene Publishing and Wiley-Interscience, New York, 1995) and Sambrook et al. (*Molecular Cloning: A Laboratory Manual*, 2$^{nd}$ ed., Cold Spring Harbor Laboratory Press, Plainview, N.Y., 1989).

As set out above, the method of the present invention contemplates the specific or preferential expression of a nucleotide sequence of interest in a reproduction-associated plant part. As used herein, "specifically expressing" means that the nucleotide sequence of interest is expressed substantially only in a reproduction-associated part of a plant. "Preferentially expressing" should be understood to mean that nucleotide sequence of interest is expressed at a higher level in a reproduction-associated part of a plant than in one or more other tissues of the plant, eg. leaf tissue or root tissue. Preferential expression in a reproduction-associated plant part may include, for example, expression of a nucleotide sequence of interest in a reproduction-associated plant part at a level of at least twice, at least 5 times or at least 10 times the level of expression seen in at least one other tissue of the plant.

As referred to herein, "expression of an operably connected nucleotide sequence in a reproduction-associated plant part" refers to the transcription and/or translation of a nucleotide sequence in one or more cells of a reproduction-associated plant part. This definition in no way implies that expression of the nucleotide sequence must occur in all cells of the reproduction-associated plant part.

The present invention contemplates expression of a nucleotide sequence of interest in a reproduction-associated plant part in any plant species. As such, the present invention contemplates expression of a nucleotide sequence of interest in, for example, monocotyledonous angiosperm plants, dicotyledonous angiosperm plants and gymnosperm plants. However, in one embodiment, the plant comprises a monocot plant. In another embodiment, the plant comprises a cereal crop plant.

In one specific embodiment, the plant comprises a rice (*Oryza sativa*) plant.

In another specific embodiment, the plant comprises a barley (*Hordeum vulgare*) plant.

Although cells derived from monocotyledonous plants such as cereal crop plants may be used in accordance with the present invention, the present invention also contemplates the use of dicotyledonous plants. Exemplary dicotyledonous plants include, for example, *Arabidopsis* spp., *Nicotiana* spp., soybean, canola, oil seed rape, sugar beet, mustard, sunflower, potato, safflower, cassava, yams, sweet potato, other Brassicaceae such as *Thellungiella halophila*, among others.

As referred to herein, a "reproduction-associated plant part" may include any part of a plant which may be used to reproduce a plant or to fertilise a plant, and the supporting structures of such parts. As such, this term may include haploid plant parts such as male and female gametes (ie. sperm and egg cells) as well as the supporting structures of the gametes, such as pollen grains, anthers, ovaries, ovules, embryo sacs, central cells and the like. The term "reproduction-associated plant part" may also comprise euploid (eg. diploid, triploid, tetraploid or hexaploid) plant parts which are associated with plant reproduction, such as seeds and parts thereof, endosperm tissue, embryos, zygotes, regenerable dedifferentiated plant tissues (eg. callus, embryogenic callus and suspension culture) and the like.

In one embodiment, the reproduction-associated plant part comprises a plant seed.

In a further embodiment, the present invention contemplates the specific or preferential expression of a nucleotide sequence of interest in the endosperm tissue of a plant seed.

The tissues of a plant encompassed by the term "endosperm" would be readily understood by one of skill in the art. However, this term should be understood to encompass at least the nutritive tissue, characteristic of flowering plants, which nourishes the embryo. The endosperm is typically formed after the fertilization of the polar nuclei of the central cell by a sperm nucleus. In most plants the endosperm is a transient tissue absorbed by the embryo before maturity, whereas in cereals and grasses it contains storage reserves in the mature grain and is not absorbed until after germination.

Typically, in at least cereal crop plants, the "endosperm" includes at least five cell types, namely, the central starchy endosperm (CSE), the sub-aleurone layer (SAL), the aleurone layer (AL), the endosperm transfer layer (ETL) and the embryo-surrounding region (ESR). The characteristics of each of these cell types are described in detail in the review of Olsen et al. (*Trends in Plant Science* 4(7): 253-257, 1999).

In another embodiment, the present invention relates to a method for specifically or preferentially expressing a nucleotide sequence of interest in the nucellar projection in the plant seed.

The "nucellar projection" is part of the nucellus. The nucellus is a maternal tissue that surrounds the central cell from which the endosperm develops. In cereals, the nucellus consists of three main cell types, the nucellus parenchyma cells, the nucellus epidermis cells and the nucellar projection. The nucellus parenchyma cells are completely autolysed soon after fertilization, while the nucellar epidermis persists throughout most of seed development, but finally autolyses and forms the hyaline layer. Concomitant with the development of the nucellar epidermis, the nucellus cells in the ventral crease of grains differentiate into the nucellar projection. The nucellar projection is the terminal maternal tissue in a route along which nutrients are transported from the vascular tissue of the pericarp to the developing endosperm and embryo.

The ETL cell layer, which includes the crease aleurone cells, forms over the nucellar projection in cereals such as barley and wheat and is analogous to the basal endosperm transfer layer which forms over the chalazal pad in maize.

In another embodiment, the present invention relates to a method for specifically or preferentially expressing a nucleotide sequence of interest in one or more ETL cells of the seed.

In yet another embodiment, the present invention relates to a method for specifically or preferentially expressing a nucleotide sequence of interest in one or more crease aleurone cells of the seed.

The present invention contemplates the specific or preferential expression of a nucleotide sequence of interest in any plant seed. In one embodiment, however, the plant seed comprises a monocot plant seed. In another embodiment, the plant seed comprises a cereal crop plant seed.

In one specific embodiment, the plant seed is a rice (*Oryza sativa*) seed. In a further specific embodiment, the nucleotide sequence of interest is expressed in the rice (*Oryza sativa*) seed at least between 5 Days After Pollination (DAP) and 18 DAP.

In yet another specific embodiment, the plant seed is a barley (*Hordeum vulgare*) seed. In a further specific embodiment, the nucleotide sequence of interest is expressed in the barley (*Hordeum vulgare*) seed at least between 9 DAP and 35 DAP.

In another embodiment, the reproduction-associated plant part comprises an anther. In yet another embodiment, the nucleotide sequence of interest is specifically or preferentially expressed in a pollen grain of the anther. In one specific embodiment, the anther or pollen grain is a rice (*Oryza sativa*) anther or pollen grain.

As set out above, the present invention contemplates a transcriptional control sequence derived from a gene which encodes a polypeptide comprising the amino acid sequence set forth in SEQ ID NO: 1 or a homolog thereof, or a functionally active fragment or variant of said transcriptional control sequence, wherein the nucleotide sequence of interest is heterologous with respect to the transcriptional control sequence or the functionally active fragment of variant thereof. The term "heterologous with respect to the transcriptional control sequence" refers to the nucleotide sequence of interest being any nucleotide sequence other than that which the transcriptional control sequence (or functionally active fragment or variant thereof) is operably connected to in its natural state.

For example, in its natural state, SEQ ID NO: 3 is operably connected to the nucleotide sequence set forth in SEQ ID NO: 4. Accordingly, in this example, any nucleotide sequence other than a nucleotide sequence consisting of the nucleotide sequence set forth in SEQ ID NO: 4 should be considered heterologous with respect to SEQ ID NO: 3.

In accordance with the definition above, it would be recognised that a nucleotide sequence of interest which is heterologous to the transcriptional control sequence (or functionally active fragment or variant thereof) may be derived from the same species as the transcriptional control sequence (or functionally active fragment or variant thereof) or from a different species.

As set out above, the present invention is predicated, in part, on effecting transcription of the nucleotide sequence of interest under the transcriptional control of a transcriptional control sequence. In one embodiment, this is effected by introducing a nucleic acid molecule comprising the transcriptional control sequence, or a functionally active fragment or variant thereof, into a cell of the plant, such that the nucleotide sequence of interest is operably connected to the transcriptional control sequence.

The nucleic acid molecule may be introduced into the plant via any method known in the art. For example, an explant or cultured plant tissue may be transformed with a nucleic acid molecule, wherein the explant or cultured plant tissue is subsequently regenerated into a mature plant including the nucleic acid molecule; a nucleic acid may be directly transformed into a plant seed, either stably or transiently; a nucleic acid may be introduced into a seed via plant breeding using a parent plant that carries the nucleic acid molecule; and the like.

In one embodiment, the nucleic acid molecule is introduced into a plant cell via transformation. Plants may be transformed using any method known in the art that is appropriate for the particular plant species. Common methods include *Agrobacterium*-mediated transformation, microprojectile bombardment based transformation methods and direct DNA uptake based methods. Roa-Rodriguez et al. (*Agrobacterium-mediated transformation of plants*, 3$^{rd}$ Ed. CAMBIA Intellectual Property Resource, Canberra, Australia, 2003) review a wide array of suitable *Agrobacterium*-mediated plant transformation methods for a wide range of plant species. Other bacterial-mediated plant transformation methods may also be utilized, for example, see Broothaerts et al. (*Nature* 433: 629-633, 2005). Microprojectile bombardment may also be used to transform plant tissue and methods for the transformation of plants, particularly cereal plants, and such methods are reviewed by Casas et al. (*Plant Breeding Rev.* 13: 235-264, 1995). Direct DNA uptake transformation protocols such as protoplast transformation and electroporation are described in detail in Galbraith et al. (eds.), *Methods in Cell Biology* Vol. 50, Academic Press, San Diego, 1995). In addition to the methods mentioned above, a range of other transformation protocols may also be used. These include infiltration, electroporation of cells and tissues, electroporation of embryos, microinjection, pollen-tube pathway, silicon carbide- and liposome mediated transformation. Methods such as these are reviewed by Rakoczy-Trojanowska (*Cell. Mol. Biol. Lett.* 7: 849-858, 2002). A range of other plant transformation methods may also be evident to those of skill in the art and, accordingly, the present invention should not be considered in any way limited to the particular plant transformation methods exemplified above.

As set out above, the transcriptional control sequence of the present invention is introduced into a plant cell such that the nucleotide sequence of interest is operably connected to the transcriptional control sequence. The present invention contemplates any method to effect this. For example, the transcriptional control sequence and a nucleotide sequence of interest may be incorporated into a nucleic acid molecule such that they are operably connected and this construct may be introduced into the target cell. In another example, the nucleic acid sequence of the present invention may be inserted into the genome of a target cell such that it is placed in operable connection with an endogenous nucleic acid sequence. As would be recognised by one of skill in the art, the insertion of the transcriptional control sequence into the genome of a target cell may be either by non-site specific insertion or by site-specific insertion (for an example of site-specific insertion see Terada et al., *Nat Biotechnol* 20:1030-1034, 2002).

The nucleotide sequence of interest, which is placed under the regulatory control of the transcriptional control sequence of the present invention, may be any nucleotide sequence of interest. For example, general categories of nucleotide sequences of interest may include nucleotide sequences which encode: reporter proteins, such as, GUS, GFP and the like; proteins involved in cellular metabolism such as Zinc finger proteins, kinases, heat shock proteins and the like; proteins involved in agronomic traits such as disease or pest resistance or herbicide resistance; proteins involved in grain characteristics such as grain biomass, nutritional value, post-harvest characteristics and the like; heterologous proteins, such as proteins encoding heterologous enzymes or structural proteins or proteins involved in biosynthetic pathways for heterologous products; "terminator" associated proteins such as barnase, barstar or diphtheria toxin. Furthermore, the nucleotide sequence of interest may alternatively encode a non-translated RNA, for example an siRNA, miRNA, antisense RNA and the like.

In a second aspect, the present invention provides a nucleic acid construct comprising a nucleotide sequence selected from the list consisting of:
 a nucleotide sequence defining a transcriptional control sequence derived from a gene which encodes a polypeptide comprising the amino acid sequence set forth in SEQ ID NO: 1 or a homolog thereof; and
 a nucleotide sequence defining a functionally active fragment or variant of said transcriptional control sequence.

The nucleic acid construct of the present invention may comprise any polyribonucleotide or polydeoxyribonucleotide, which may be unmodified RNA or DNA or modified RNA or DNA. For example, the nucleic acid construct of the invention may comprise single- and/or double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the nucleic acid construct may comprise triple-stranded regions comprising RNA or DNA or both RNA and DNA. The nucleic acid construct may also comprise one or more modified bases or DNA or RNA backbones modified for stability or for other reasons. "Modified" bases include, for example, tritylated bases and unusual bases such as inosine. A variety of modifications can be made to DNA and RNA; thus the term "nucleic acid construct" embraces chemically, enzymatically, or metabolically modified forms.

In one embodiment, the nucleic acid construct comprises DNA. Accordingly, the nucleic acid construct of the present invention may comprise, for example, a linear DNA molecule, a plasmid, a transposon, a cosmid, an artificial chromosome and the like. Furthermore, the nucleic acid construct of the present invention may be a separate nucleic acid molecule or may be a part of a larger nucleic acid molecule.

In further embodiments, the transcriptional control sequence is derived from a gene which encodes a polypeptide comprising the amino acid sequence set forth in SEQ ID NO: 1 or SEQ ID NO: 5, or a homolog of either of the foregoing amino acid sequences.

In another embodiment, the transcriptional control sequence is derived from a plant. In yet another embodiment, the transcriptional control sequence is derived from a rice (*Oryza sativa*) plant.

In yet another embodiment, the transcriptional control sequence is derived from a gene which comprises an open reading frame comprising the nucleotide sequence set forth in SEQ ID NO: 2.

In one specific embodiment, the transcriptional control sequence comprises the nucleotide sequence set forth in SEQ ID NO: 3 or a functionally active fragment or variant thereof.

In a further embodiment, the nucleic acid construct further comprises a nucleotide sequence of interest that is heterologous with respect to the transcriptional control sequence or the functionally active fragment or variant thereof; wherein the nucleotide sequence of interest is operably connected to the transcriptional control sequence or functionally active fragment or variant thereof.

In another embodiment, the nucleic acid construct may further comprise a nucleotide sequence defining a transcription terminator.

The term "transcription terminator" or "terminator" refers to a DNA sequence at the end of a transcriptional unit which signals termination of transcription. Terminators are 3'-non-translated DNA sequences generally containing a polyadenylation signal, which facilitates the addition of polyadenylate sequences to the 3'-end of a primary transcript. As with promoter sequences, the terminator may be any terminator sequence which is operable in the cells, tissues or organs in which it is intended to be used. Examples of suitable terminator sequences which may be useful in plant cells include: the nopaline synthase (nos) terminator, the CaMV 35S terminator, the octopine synthase (ocs) terminator, potato proteinase inhibitor gene (pin) terminators, such as the pinII and pinIII terminators and the like.

In one specific embodiment, the nucleic acid construct comprises an expression cassette comprising the structure:

$$([N]_w\text{-TCS-}[N]_x\text{-SoI-}[N]_y\text{-TT-}[N]_z)$$

wherein:
$[N]_w$ comprises one or more nucleotide residues, or is absent;
TCS defines a transcriptional control sequence derived from a gene which encodes either a polypeptide comprising the amino acid sequence set forth in SEQ ID NO: 1 or a homolog thereof; or a functionally active fragment or variant of said transcriptional control sequence;
$[N]_x$ comprises one or more nucleotide residues, or is absent;
SoI comprises a nucleotide sequence of interest that encodes an mRNA or non-translated RNA, wherein SoI is heterologous to, and operably connected to, TCS;
$[N]_y$ comprises one or more nucleotide residues, or is absent;
TT comprises a nucleotide sequence defining a transcription terminator;
$[N]_z$ comprises one or more nucleotide residues, or is absent.

The nucleic acid constructs of the present invention may further comprise nucleotide sequences as desired. For example, the nucleic acid construct may include an origin of replication for one or more hosts; a selectable marker gene which is active in one or more hosts and the like.

As used herein, the term "selectable marker gene" includes any gene that confers a phenotype on a cell, in which it is expressed, to facilitate the identification and/or selection of cells which are transfected or transformed with a nucleic acid construct of the invention.

A range of nucleotide sequences encoding suitable selectable markers are known in the art. Exemplary nucleotide sequences that encode selectable markers include: antibiotic resistance genes such as ampicillin-resistance genes, tetracycline-resistance genes, kanamycin-resistance genes, the AURI-C gene which confers resistance to the antibiotic aureobasidin A, neomycin phosphotransferase genes (eg. nptI and nptII) and hygromycin phosphotransferase genes (eg. hpt); herbicide resistance genes including glufosinate, phosphinothricin or bialaphos resistance genes such as phosphinothricin acetyl transferase encoding genes (eg. bar), glyphosate resistance genes including 3-enoyl pyruvyl shikimate 5-phosphate synthase encoding genes (eg. aroA), bromyxnil resistance genes including bromyxnil nitrilase encoding genes, sulfonamide resistance genes including dihydropterate synthase encoding genes (eg. sul) and sulfonylurea resistance genes including acetolactate synthase encoding genes; enzyme-encoding reporter genes such as GUS and chloramphenicolacetyltransferase (CAT) encoding genes; fluorescent reporter genes such as the green fluorescent protein-encoding gene; and luminescence-based reporter genes such as the luciferase gene, amongst others.

The present invention extends to all genetic constructs substantially as described herein, which may include further nucleotide sequences intended for the maintenance and/or replication of the genetic construct in prokaryotes or eukaryotes and/or the integration of the genetic construct or a part thereof into the genome of a eukaryotic or prokaryotic cell.

In one embodiment, the construct of the invention is adapted to be at least partially transferred into a plant cell via *Agrobacterium*-mediated transformation. Accordingly, in one specific embodiment, the nucleic acid construct of the present invention comprises left and/or right T-DNA border sequences.

Suitable T-DNA border sequences would be readily ascertained by one of skill in the art. However, the term "T-DNA border sequences" should be understood to encompass any substantially homologous and substantially directly repeated nucleotide sequences that delimit a nucleic acid molecule that is transferred from an *Agrobacterium* sp. cell into a plant cell susceptible to *Agrobacterium*-mediated transformation. By way of example, reference is made to the paper of Peralta and Ream (*Proc. Natl. Acad. Sci. USA,* 82(15): 5112-5116, 1985) and the review of Gelvin (*Microbiology and Molecular Biology Reviews,* 67(1): 16-37, 2003).

In further embodiments, the present invention also contemplates any suitable modifications to the genetic construct which facilitate bacterial mediated insertion into a plant cell via bacteria other than *Agrobacterium* sp., for example, as described in Broothaerts et al. (2005, supra).

Those skilled in the art will be aware of how to produce the constructs described herein and of the requirements for obtaining the expression thereof, when so desired, in a specific cell or cell-type under the conditions desired. In particular, it will be known to those skilled in the art that the genetic manipulations required to perform the present invention may require the propagation of a genetic construct described herein or a derivative thereof in a prokaryotic cell such as an *E. coli* cell or a plant cell or an animal cell. Exemplary methods for cloning nucleic acid molecules are described in Sambrook et al. (*Molecular Cloning: A Laboratory Manual,* Cold Spring Harbor Laboratory Press, New York, 2000).

In a third aspect, the present invention provides a cell comprising a nucleic acid construct of the second aspect of the invention or a genomically integrated form thereof.

The nucleic acid construct may be maintained in the cell as a nucleic acid molecule, as an autonomously replicating genetic element (eg. a plasmid, cosmid, artificial chromosome or the like) or it may be integrated into the genomic DNA of the cell.

As used herein, the term "genomic DNA" should be understood in its broadest context to include any and all endogenous DNA that makes up the genetic complement of a cell. As such, the genomic DNA of a cell should be understood to include chromosomes, mitochondrial DNA, plastid DNA, chloroplast DNA, endogenous plasmid DNA and the like. As such, the term "genomically integrated" contemplates chromosomal integration, mitochondrial DNA integration, plastid DNA integration, chloroplast DNA integration, endogenous plasmid integration, and the like.

The cells contemplated by the third aspect of the invention include any prokaryotic or eukaryotic cell. In some embodiments, the cell is a plant cell, a monocot plant cell, a cereal crop plant cell and/or a rice (*Oryza sativa*) cell or a barley (*Hordeum vulgare*) cell.

In another embodiment, the cell may comprise a prokaryotic cell. For example, the prokaryotic cell may include an *Agrobacterium* sp. cell (or other bacterial cell), which carries the nucleic acid construct and which may, for example, be used to transform a plant. In another exemplary embodiment, the prokaryotic cell may be an *E. coli* cell, which may, for example, be used in the construction or cloning of the nucleic acid construct.

In a fourth aspect, the present invention contemplates a multicellular structure comprising one or more cells of the third aspect of the invention.

In one embodiment, the multicellular structure comprises a plant or a part, organ or tissue thereof.

As referred to herein, "a plant or a part, organ or tissue thereof" should be understood to specifically include a whole plant; a plant tissue; a plant organ; a plant part; reproduction-associated plant parts (as defined herein); and cultured plant tissue such as a callus or suspension culture.

In one embodiment, the plant or a part, organ or tissue thereof comprises a monocot plant or a part, organ or tissue thereof. In further embodiments, the plant or a part, organ or tissue thereof comprises a cereal crop plant or a part, organ or tissue thereof or a rice (*Oryza sativa*) or barley (*Hordeum vulgare*) plant or a part, organ or tissue thereof.

In some embodiment, the multicellular structure comprises a reproduction-associated plant part.

In a further embodiment, the multicellular structure comprises a plant seed.

A nucleotide sequence of interest may be operably connected to the transcriptional control sequence or the functionally active fragment or variant thereof, such that the nucleotide sequence of interest is specifically or preferentially expressed in the plant seed. In some embodiments, the nucleotide sequence of interest is specifically or preferentially expressed in any of the endosperm tissue, nucellar projection, ETL cells or crease aleurone cells of the plant seed.

The multicellular structure may comprise any plant seed. In one embodiment, the plant seed comprises a monocot plant seed. In another embodiment, the plant seed comprises a cereal crop plant seed.

In one specific embodiment, the plant seed is a rice (*Oryza sativa*) seed. In a further specific embodiment, a nucleotide sequence of interest is expressed in the rice (*Oryza sativa*) seed at least between 5 DAP and 18 DAP.

In another specific embodiment, the plant seed is a barley (*Hordeum vulgare*) seed. In a further specific embodiment, a nucleotide sequence of interest is expressed in the barley (*Hordeum vulgare*) seed at least between 9 DAP and 35 DAP.

In yet another embodiment, the multicellular structure comprises an anther.

A nucleotide sequence of interest may be operably connected to the transcriptional control sequence or the functionally active fragment or variant thereof, such that the nucleotide sequence of interest is specifically or preferentially expressed in the anther. The nucleotide sequence of interest may also be specifically or preferentially expressed in a pollen grain of the anther.

In one specific embodiment, the anther or pollen grain is a rice (*Oryza sativa*) anther or pollen grain.

In a fifth aspect, the present invention provides an isolated nucleic acid molecule comprising a nucleotide sequence defining:
    a transcriptional control sequence derived from a gene which encodes a polypeptide comprising the amino acid sequence set forth in SEQ ID NO: 1 or a homolog thereof; or a functionally active fragment or variant of said transcriptional control sequence.

The isolated nucleic acid molecule of the present invention may comprise any polyribonucleotide or polydeoxyribonucleotide, which may be unmodified RNA or DNA or modified RNA or DNA. For example, the isolated nucleic acid molecules of the invention may comprise single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the isolated nucleic acid molecules may comprise triple-stranded regions comprising RNA or DNA or both RNA and DNA. The isolated nucleic acid molecules may also contain one or more modified bases or DNA or RNA backbones modified for stability or for other reasons. "Modified" bases include, for example, tritylated bases and unusual bases such as inosine. A variety of modifications can be made to DNA and RNA; thus the term "nucleic acid" includes unmodified nucleic acids as well as chemically, enzymatically, or metabolically modified forms.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. An "isolated" nucleic acid molecule should also be understood to include a synthetic nucleic acid molecule, including those produced by chemical synthesis using known methods in the art or by in-vitro amplification (eg. polymerase chain reaction and the like).

In further embodiments, the transcriptional control sequence is derived from a gene which encodes a polypeptide comprising the amino acid sequence set forth in SEQ ID NO: 1, SEQ ID NO: 5, or a homolog of either of the foregoing amino acid sequences.

In another embodiment, the transcriptional control sequence is derived from a plant. In yet another embodiment, the transcriptional control sequence is derived from a rice (*Oryza sativa*) plant.

In yet another embodiment, the transcriptional control sequence is derived from a gene which comprises an open reading frame comprising the nucleotide sequence set forth in SEQ ID NO: 2.

In one specific embodiment, the transcriptional control sequence comprises the nucleotide sequence set forth in SEQ ID NO: 3 or a functionally active fragment or variant thereof.

Generally, the transcriptional control sequence specifically or preferentially directs the expression of an operably connected nucleotide sequence in a reproduction-associated plant part.

In one embodiment, the reproduction-associated plant part comprises a plant seed. In another embodiment, the transcriptional control sequence specifically or preferentially directs the expression of an operably connected nucleotide sequence in any of the endosperm tissue, nucellar projection, ETL cells and/or crease aleurone cells of the plant seed.

As set out above, the transcriptional control sequence may effect specific or preferential expression in a seed from any plant species. However, in one embodiment the plant is a monocot plant. In another embodiment, the plant is a cereal crop plant.

In one specific embodiment, the plant seed is a rice (*Oryza sativa*) seed. In a further specific embodiment, the transcriptional control sequence specifically or preferentially directs the expression of an operably connected nucleotide sequence in a rice (*Oryza sativa*) seed at least between 5 DAP and 18 DAP.

In another specific embodiment, the plant seed is a barley (*Hordeum vulgare*) seed. In a further specific embodiment, the transcriptional control sequence specifically or preferentially directs the expression of an operably connected nucleotide sequence in a barley (*Hordeum vulgare*) seed at least between 9 DAP and 35 DAP.

In another embodiment, the reproduction-associated plant part comprises an anther. In this embodiment, the transcriptional control sequence may specifically or preferentially direct the expression of an operably connected nucleotide sequence in a pollen grain of the anther. In one specific embodiment, the anther or pollen grain is a rice (*Oryza sativa*) anther or pollen grain.

Finally, reference is made to standard textbooks of molecular biology that contain methods for carrying out basic techniques encompassed by the present invention, including DNA restriction and ligation for the generation of the various genetic constructs described herein. See, for example, Maniatis et al., *Molecular Cloning: A Laboratory Manual* (Cold Spring Harbor Laboratory Press, New York, 1982) and Sambrook et al. (2000, supra).

The present invention is further described by the following non-limiting examples:

BRIEF DESCRIPTION OF THE FIGURES

FIG. 2 shows a multiple sequence alignment between the wheat WENDL9 amino acid sequence and the rice OsWENDL9L amino acid sequence (SEQ ID NO: 1). Identical amino acids are in black boxes, similar amino acids are in grey boxes. Identity positions: 26.1%; consensus positions: 36.4%

FIG. 3 shows the genomic nucleotide sequence of the OsWENDL9L gene (SEQ ID NO: 4) including the OsPR9a transcriptional control sequence (SEQ ID NO: 3), the untranslated regions, the coding sequence (SEQ ID NO: 2) and the encoded amino acid sequence (SEQ ID NO: 1). The transcriptional control sequence is shown in black, the coding sequence is shown in bold (with the encoded amino acid sequence over) and the untranslated regions (UTRs) are underlined (the identification of the UTRs is based on EST CA760707).

FIG. 8 shows a restriction map of vector pMDC164-OsPR9a.

EXAMPLE 1

Plant Material and Growth Conditions

*Oryza sativa* ssp. *japonica* cv. Nipponbare was used for genomic DNA isolation and for the subsequent cloning of the OsPR9a promoter (SEQ ID NO: 3).

*Hordeum vulgare* cv Golden Promise was used for transformation using *Agrobacterium tumefaciens*.

EXAMPLE 2

Isolation of Promoter Sequences and Preparation of Reporter Constructs

A wheat cDNA, designated WENDL9, was isolated from a cDNA library prepared from the liquid part of the endosperm at 3-6 DAP.

Northern blotting and Q-PCR were subsequently used to determine the expression pattern of WENDL9. The Northern blotting was performed according to the method described in Sambrook et al. (2000, supra).

Q-PCR was also performed according to the method described in Burton et al. (*Plant Physiol.* 134:224-236, 2004) and Vandesompele et al. (*Genome Biol.* 3: research0034.1-0034.11, 2002) using the following primers:

TABLE 2

| Primer sequences used for Q-PCR | | |
|---|---|---|
| Primer | Sequence | Sequence Identifier |
| QPCRf | 5'-GCACAATCAGTGTTGTTGTGC-3' | SEQ ID NO: 7 |
| QPCRr | 5'-GTGGACCAGACAACACAAGAG-3' | SEQ ID NO: 8 |

Figure 1:
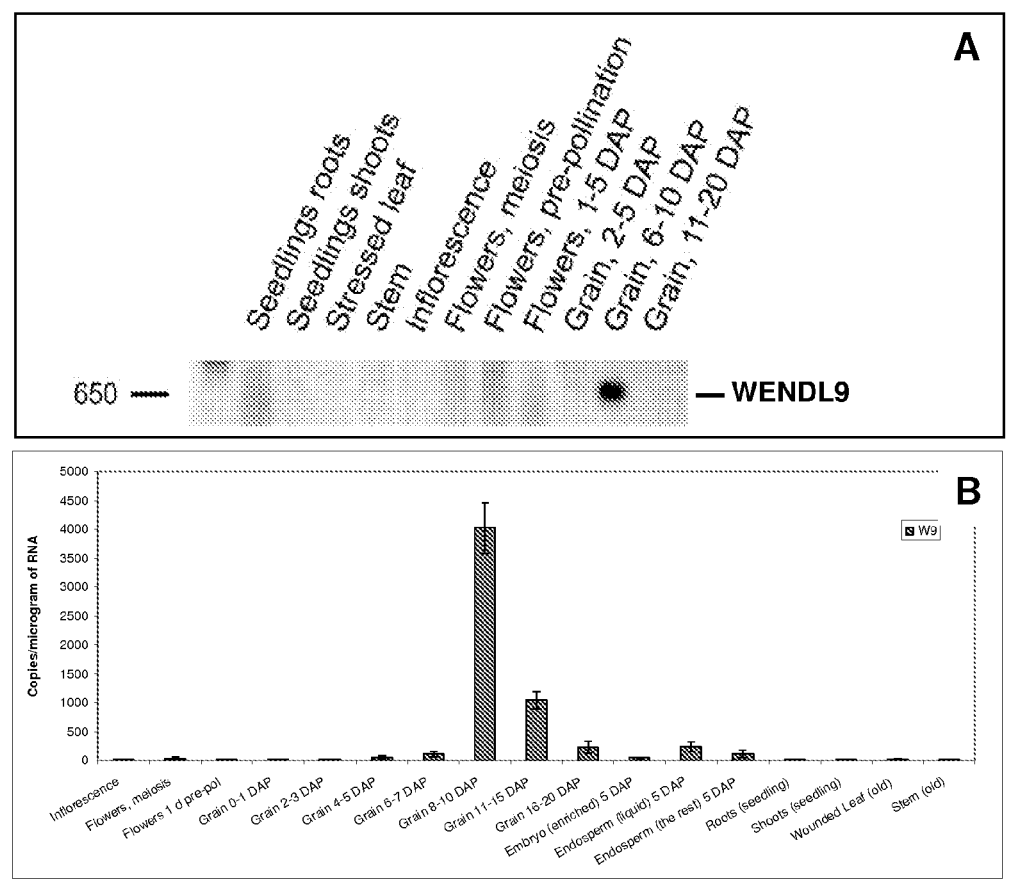
FIG. 1 shows the seed (endosperm) specific expression of WENDL9 (Wheat Endosperm Library clone 9), as demonstrated by Northern blot hybridization (Panel A) and Q-PCR (Panel B).

As shown in FIG. 1, both the northern blot analysis and Q-PCR demonstrated substantially specific WENDL9 expression in the endosperm.

The amino acid sequence encoded by the wheat WENDL9 cDNA was deduced and was then used to identify rice orthologs in the NCBI and TIGR EST databases using the TBLASTN algorithm. A rice EST, Accession No. CA760707 (SEQ ID NO: 2), originating from a rice panicle cDNA library, was identified as encoding a homolog of the wheat WENDL9 polypeptide. The amino acid sequence encoded by SEQ ID NO: 2 was deduced and this amino acid sequence was designated as SEQ ID NO: 1.

An alignment of the SEQ ID NO: 1 amino acid sequence and the amino acid sequence encoded by the wheat WENDL9 cDNA is shown in FIG. 2.

The EST sequence (SEQ ID NO: 2) was also used to query genomic database of rice. A genomic nucleotide sequence exhibiting complementarity to the OsWENDL9L cDNA sequence set forth in SEQ ID NO: 2 was identified. The OsWENDL9L genomic nucleotide sequence is shown in FIG. 3, wherein the transcriptional control sequence, untranslated regions, coding region and encoded amino acid sequence are shown. The genomic nucleotide sequence (coding and intronic sequences) of the OsWENDL9L gene is designated herein as SEQ ID NO: 4.

A transcriptional control sequence (including a promoter), comprising the full-length 5'-untranslated region of the identified OsWENDL9L gene, was identified and designated as OsPR9a (SEQ ID NO: 3).

The OsPR9a promoter sequence was isolated by PCR using AccuPrime™ Pfx DNA polymerase (Invitrogen) and rice genomic DNA as a template. The PCR product was directionally cloned into the pENTR-D-TOPO vector using pENTR Directional TOPO Cloning Kits (Invitrogen).

TABLE 3

| Primer sequences used for sequencing and PCR amplification | | |
|---|---|---|
| Primer | Sequence | Sequence Identifier |
| C_PR9a | 5'-GTTCTTCAGGGACGAAAATGATACTCC-3' | SEQ ID NO: 9 |
| PR9r | 5'-ATTAGATGATTTATAACACAATCTTATCTAC-3' | SEQ ID NO: 10 |
| GUS5'rev | 5'-ACTGAATGCCCACAGGCCGT-3' | SEQ ID NO: 11 |

The construct was linearized with either EcoRV or MluI restriction enzymes and used for cloning of the promoter by recombination into the destination binary vector for plant transformation, pMDC164 (Curtis and Grossniklaus, *Plant Physiol.* 133: 462-469, 2003), upstream of a β-glucoronidase (GUS) cDNA.

These constructs were subsequently used for rice and barley transformation.

EXAMPLE 3

Plant Transformation (i) Rice Transformation

Figure 8:
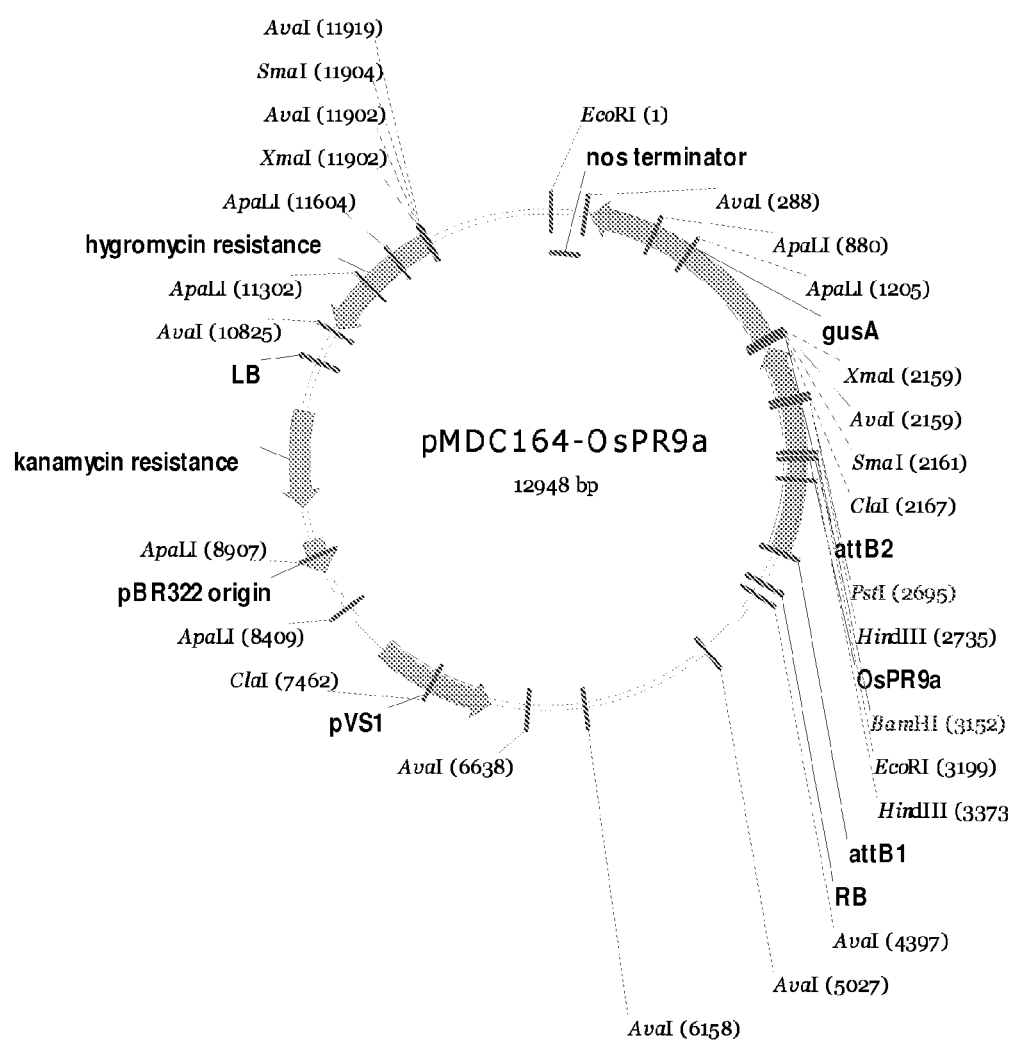

Five-week-old secondary, seed embryo-derived callus of cv. Nipponbare (*Oryza sativa* ssp. *japonica*) was co-cultured with the *Agrobacterium* strain EHA105 or LBA4404 carrying the pMDC164-OsPR9a (FIG. 8) binary plasmid following the procedure detailed in Sallaud et al. (*Theor. Appl. Genet.* 106: 1396-1408, 2003). Dehulled seeds were sterilized, inoculated on NB medium and incubated for 18-21 days in the dark as described in Chen et al. (*Plant Cell Rep.* 18: 25-31, 1998). Embryogenic nodular units (0.5-1 mm long), released from the primary embryo scutellum-derived callus at the explant/ medium interface, were transferred onto fresh NB medium and incubated for an additional 10-15 days depending on the variety.

Between 50 and 100 3- to 5-mm-long embryogenic nodular units were immersed into 25 ml of liquid co-culture medium (CCL) containing *Agrobacterium* cells at a density of $3$-$5 \times 10^9$ cells ml$^{-1}$ (OD600=1) in a 100-mm diameter petri dish for 10-15 min. Ten callus pieces were then blotted dry on sterilized filter paper, transferred to a petri dish containing solid co-culture medium (CCS) and incubated for 3 days at 25° C. in the dark. Five to seven uncontaminated co-cultured calli were then individually transferred to one dish of R2S (Ohira et al., *Plant & Cell Physiol.* 14: 1113-1121, 1973) selection medium, which contained hygromycin for selection of transformed tissues and cefotaxime and vancomycin for eliminating *Agrobacterium*, and incubated at 27° C. in the dark.

Following 2 weeks of selection on R2S medium, the calli were transferred to NBS medium. After 1 week of incubation, the protuberances developed into brownish globular structures, which were gently teased apart with forceps on the medium around the original callus and incubated for 10-15 days in the resealed petri dish. Five weeks after co-culture, the globular structures had evolved into round shaped, compact, opaque and yellowish calli. The putatively transgenic, hygromycin-resistant calli were gently picked out, placed on the PRAG pre-regeneration medium and incubated for a further week. All of the resistant calli originating from a single co-cultured embryogenic nodular unit were grouped in a sector of the PRAG dish, which can accommodate 40-50 resistant calli.

Four to five, creamy-white, lobed calli with a smooth and dry appearance were individually transferred to one dish of RN regeneration medium, kept for 2 days in the dark, then maintained for 3 weeks under a 12/12-h (day/night) photoperiod. Shoots regenerating from a resistant callus were dissected and sub-cultured in test tubes containing P medium for a further 3-week growth period to promote vigorous tiller and root development before being transferred to Jiffy peat pellets in the containment greenhouse for acclimatization.

All of the media referred to above are as described in Sallaud et al. (2003, supra).

(ii) Barley Transformation

*Agrobacterium tumefaciens*-mediated transformation of barley (*Hordeum vulgare* cv Golden Promise) was performed with plasmid pMDC164-OsPR9a using the procedure developed by Tingay et al. (*Plant J.* 11: 1369-1376, 1997) and modified by Matthews et al. (*Mol. Breed.* 7:195-202, 2001).

Developing spikes were harvested from donor plants grown in the glasshouse when the immature embryos are approximately 1-2 mm in diameter. The immature embryos were aseptically excised from the surface-sterilised grain, and the scutella were isolated by removing the embryonic axes.

Twenty five freshly isolated scutella were cultured cut side-up in the centre of a 90 mm×10 mm Petri dish containing callus induction medium, based on the recipe of Wan and Lemaux (*Plant Physiol.* 104: 37-48, 1994). This medium is composed of MS macro-nutrients (Murashige and Skoog, *Physiol. Plant.* 15: 473-497, 1962), FHG micro-nutrients (Hunter, *Plant regeneration from microspores of barley, Hordeum vulgare*, Ph-D thesis, Wye College, University of London, Ashford, Kent, 1988), supplemented with 30 g/L maltose, 1 mg/L thiamine-HCl, 0.25 g/L myo-inositol, 1 g/L casein hydrolysate, 0.69 g/L L proline, 10 µM CuSO$_4$, 2.5 mg/L Dicamba (3,6-dichloro-o-anisic acid), and is solidified with 3.5 g/L Phytagel (Sigma Chemicals, St. Louis, Mo., USA).

*Agrobacterium* suspension (50 ml) was aliquotted onto the scutella, and the Petri dish was held at a 45° angle to drain away excess bacterial suspension. The explants were then turned over and dragged across the surface of the medium to the edge of the Petri dish. The scutella were transferred to a fresh plate of callus induction medium and cultured cut side-up for three days in the dark at 22-24° C.

Following co-cultivation, the scutella were removed to fresh callus induction medium containing 95 µM hygromycin B (Becton Dickinson Biosciences, Palo Alto, Calif., USA) and cultured in the dark. The entire callus of an individual scutellum was transferred to fresh selection medium every fortnight for a further six weeks. At the end of the callus selection period, the callus derived from each treated scutellum was transferred to shoot regeneration medium. This medium is based on the FHG recipe of Wan and Lemaux (1994, supra). It contains FHG macro- and micro-nutrients (Hunter, 1988, supra), 1 mg/L thiamine-HCl, 1 mg/L benzylaminopurine (BAP), 0.25 g/L myo-inositol, 0.73 g/L L-glutamine, 62 g/L maltose, 10 µM CuSO$_4$, 38 µM hygromycin B, and is solidified with 3.5 g/L Phytagel. The cultures were exposed to light (16 h day/8 h night photo-period) for three to four weeks at 22-24° C. The regenerated shoots were excised from the callus and transferred to culture boxes (Magenta Corporation, Chicago, Ill., USA) that contained hormone-free callus induction medium, supplemented with 95 µM hygromycin B to induce root formation.

All plant tissue culture media used after co-cultivation contained 150 mg/L Timentin (SmithKline Beecham, Pty. Ltd., Melbourne, Australia) to inhibit the growth of *Agrobacterium tumefaciens*.

The tissue culture-derived plants were finally established in soil and grown to maturity.

Figure 4:
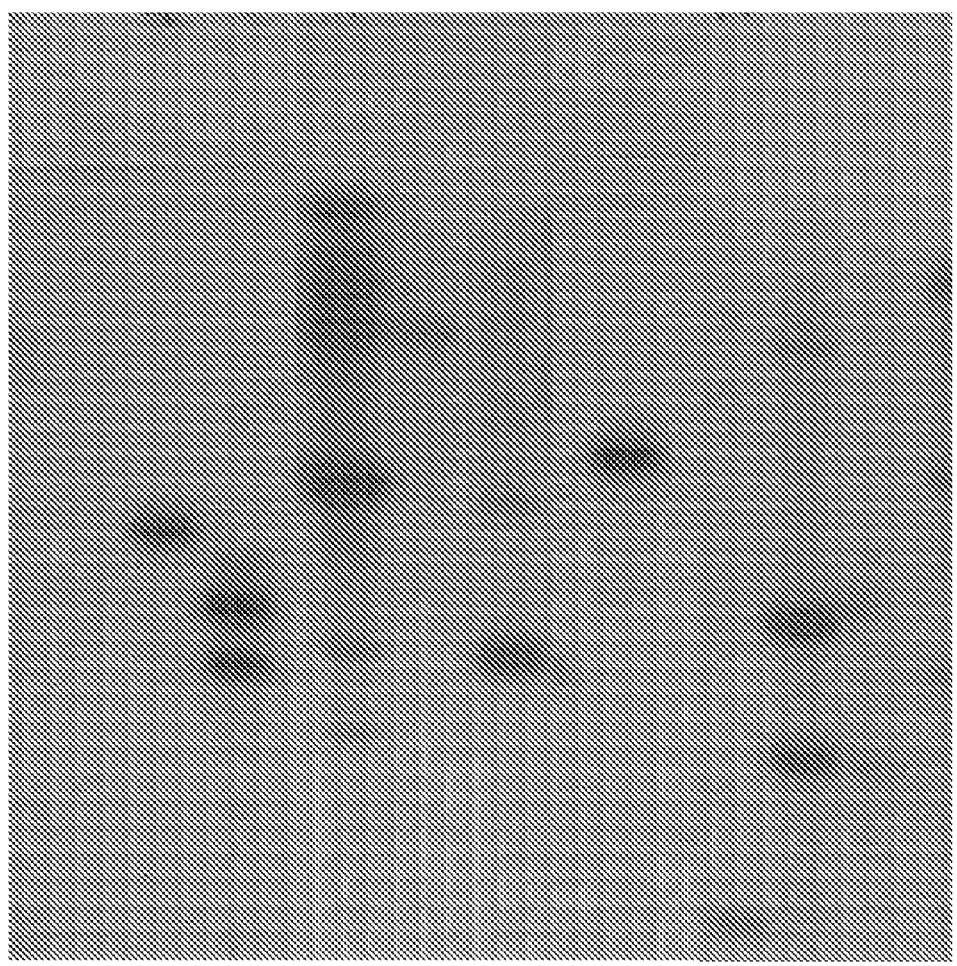
FIG. 4 shows a Southern blot indicating the copy number of OsPR9a:GUS in independent lines of transgenic barley plants. This Southern Blot confirms the successful integration of pMDC164-OsPR9a into transgenic plant lines. The XhoI fragment excised from pCAMBIA1380 vector, which contained coding region of Hygromycin phosphotransferase was used as a probe. WT-control: wild type *Hordeum vulgare* cv. Golden promise, 1-9 are lines 1-9 of transgenic plants, respectively. The number of bands reflects number of integrated copies.

Presence of inserts in transgenic lines was confirmed by Southern blot hybridization using as a probe a 1.1 kb fragment of the hygromycin phosphotransferase gene (hpt) amplified from the vector pCAMBIA1380. The results of the Southern hybridization, showing insertion of the construct in several transgenic barley lines, are shown in FIG. 4.

EXAMPLE 4

β-Glucuronidase Assays

β-glucuronidase activity in transgenic barley plants was analysed by histochemical staining using the chromogenic substrate 5-bromo-4-chloro-3-ndolyl-glucuronic acid (X-Gluc) (Bio Vectra) as described by Hull and Devic (*Methods Mol Biol.* 49: 125-41, 1995). Different plant organs, whole grain and grain sections of different ages were immersed in a 1 mM X-Gluc solution in 100 mM sodium phosphate, pH 7.0, 10 mM Na EDTA, 2 mM FeK$_3$(CN)$_6$, 2 mM K$_4$Fe(CN)$_6$ and 0.1% Triton X-100. After vacuum infiltration at ~26 in Hg for 20 min, the samples were incubated at 37° C. until satisfactory staining was observed. Tissues were incubated in 20%, 35%, 50%, fixed in FAA and cleared in 70% ethanol. The whole-mount grains were then observed under the dissecting microscope and photographs taken using a Leica digital camera equipped to the microscope. The grain samples were continued dehydrating in 80%, 90% and incubated in 95% ethanol with 0.05% of the counter stain Eosin Yellow for a better contrast. Both longitudinal and transverse sections of the tissues were embedded in paraffin wax, sectioned at 9-12 μm, de-paraffinised and mounted in DPX mountant (Fluka Biochemika) as described in Weigel and Glazebrook (*ARABIDOPSIS A Laboratory Manual*, p. 243-248, Cold Spring Harbor Laboratory Press, 2002). The specimen were observed under a compound microscope (Leica) and photographed with Leica digital camera.

EXAMPLE 5

Activity of OsPR9a Promoter in Rice and Barley

Figure 5:
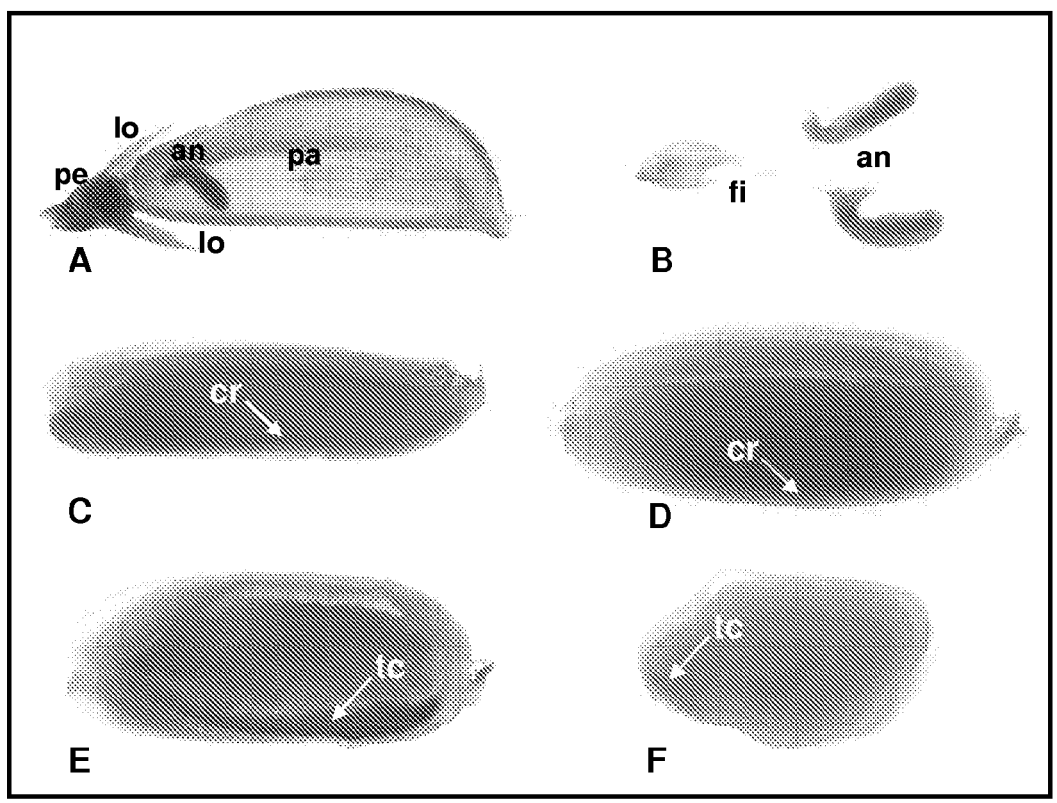
FIG. 5 shows OsPR9a promoter activity in transgenic rice plants (G35, $T_0$) as shown by histochemical GUS assay. Panels A and B show parts of the spikelet (G35, $T_0$), showing GUS expressed in anthers at anthesis; Panels C and D illustrate GUS staining in the whole-mount caryopsis at 7 DAP and 18 DAP, respectively; Panels E and F show GUS expression in the transfer cells of transverse and longitudinal cut caryopses respectively at 18 DAP. An—anther; em—embryo; en—endosperm; fi—filament; lo—lodicule; pa—palea; pe—pedicel; tc—transfer cell; d—dorsal and v—ventral side of the grain
Figure 6:
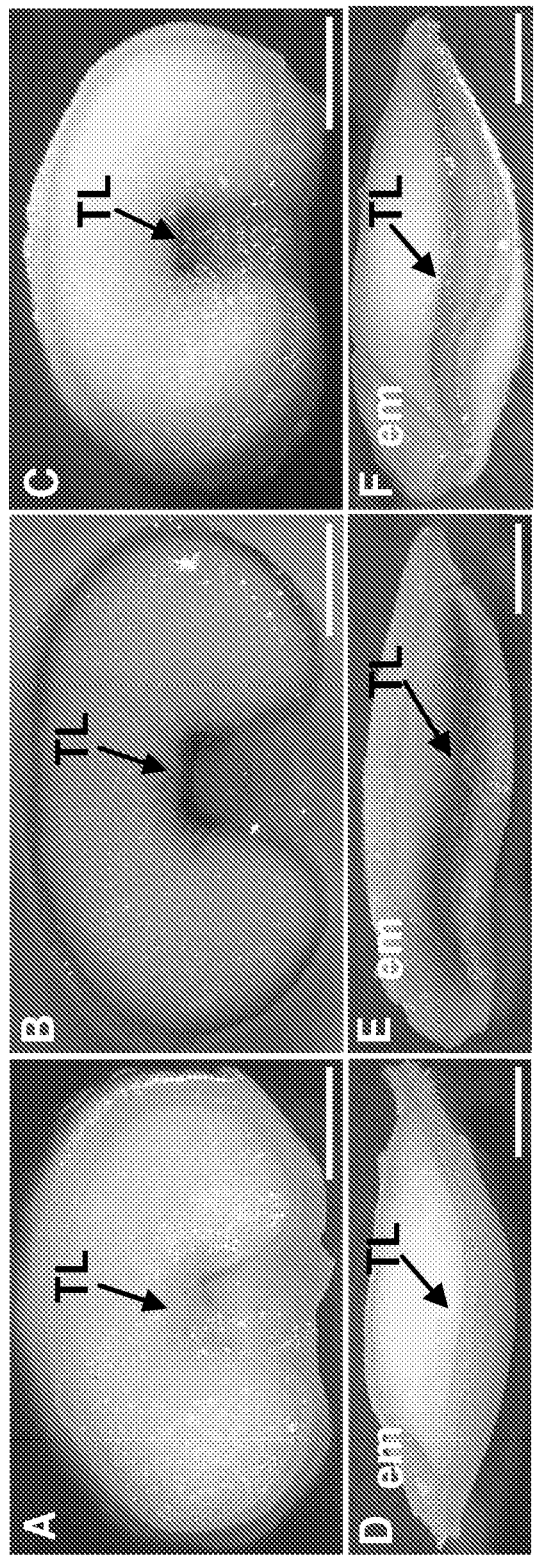
FIG. 6 shows a whole-mount GUS assay of transgenic $T_2$ barley developing grains under the control of OsPR9a promoter. GUS activity was not detected in untransformed Golden Promise caryopses shown in transverse cut at 18 DAP (A), and longitudinal cut at 20 DAP (D). GUS was expressed in the transfer cell layers of the developing caryopses demonstrated in the transverse sections at 10 DAP (B), 30 DAP (C) and, longitudinal sections at 20 DAP (E) and 30 DAP (F). em—embryo; TL—endosperm transfer cell layers. Bars=1 mm.
Figure 7:
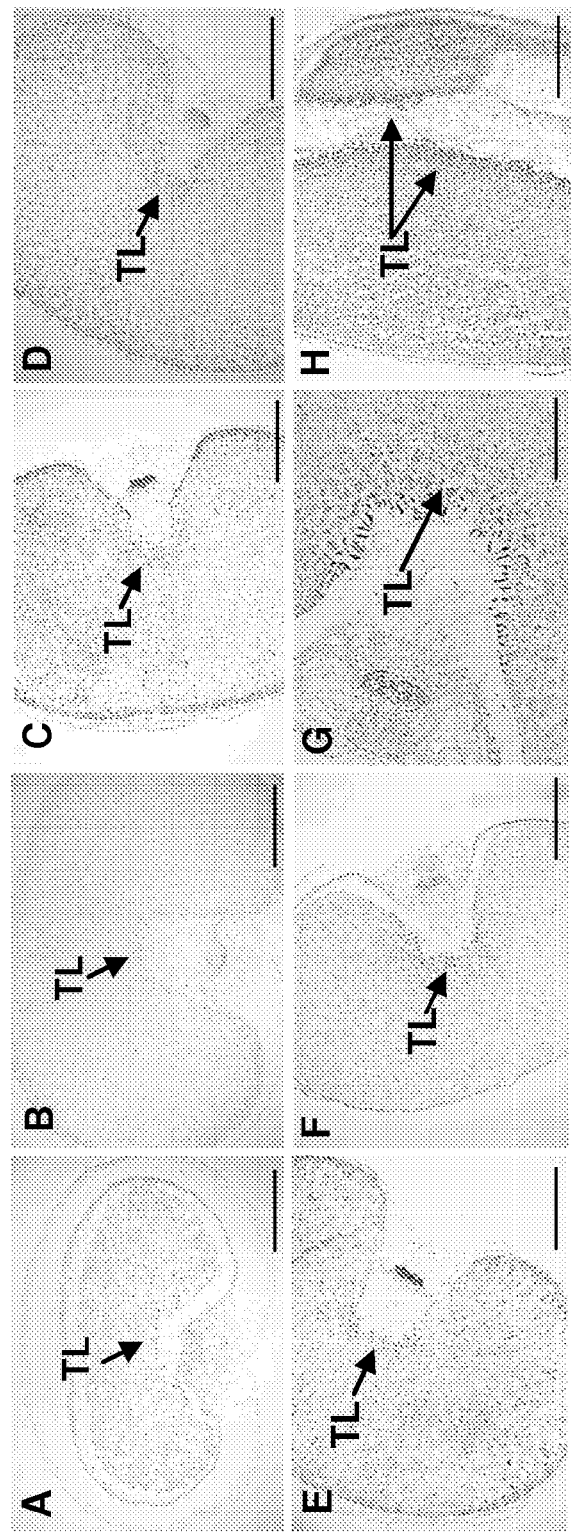
FIG. 7 shows the expression of OsPR9a:GUS in $T_2$ developing barley grains. (A) and (B)—transverse sections of caryopses from an untransformed barley plant at 10 and 20 DAP, respectively. (C)-(F)— transverse sections of caryopses from transgenic OsPR9a:GUS at 12, 16, 20 and 25 DAP, respectively. (G)—transverse section of a caryopsis from OsPR9a:GUS plant at 25 DAP. (H)—longitudinal section of a caryopsis from OsPR9a:GUS at 25 DAP. Bars in A to F and H=10 mm; bar in G=25 mm. TL—endosperm transfer cell layers.

Two agriculturally important crop plants, rice and barley, were used to determine the expression pattern of the OsPR9a (SEQ ID NO: 3) promoter.
(i) Promoter Activity in Rice (*Oryza sativa*)
Five putative transgenic rice lines were obtained from OsPR9a:GUS construct. Root, stems, leaf tip, leaf blade, sheath, collar, floret and developing grains from anthesis to mature stages were collected and histochemical GUS assays were performed.
As shown in FIG. 5, promoter activity was observed in OsPR9a:GUS transformed $T_0$ lines GUS activity was predominantly expressed in the endosperm transfer cells from 5 DAP till 18 DAP, with a peak at 11 DAP. GUS activity was also observed in mature pollen at anthesis (Panels A and B). No GUS activity was detected in other tissues throughout the growth stages.
(ii) Promoter Activity in Barley (*Hordeum vulgare*)
All barley transformants were confirmed with Southern blot hybridization (FIG. 4). Tissue samples, i.e. leaf, root, culm, spikelet, floret, rachis and developing caryopsis from pollination to mature stages were harvested and assayed for GUS activity. GUS activity was observed in three putative transgenic barley $T_0$ lines. Among these lines, G35-2 showed particularly strong GUS activity and its $T_2$ progenies were also analysed as shown in FIG. 6 and FIG. 7.

The whole-mount (FIG. 6) and histological GUS (FIG. 7) assays revealed that the promoter activity retained in the endosperm transfer cell layers and the adjacent starchy endosperm cells above the nucellar projection (FIG. 6B, C, E, F and FIG. 7C-7H) from 9 DAP till at least 35 DAP, with especially strong expression between 12 DAP to 25 DAP. FIG. 7D shows a higher magnification of GUS expression in the region of transfer layers and the neighbouring central starchy endosperm cells. GUS activity was not observed in the untransformed barley grains at various developing stages as shown in FIG. 6A, 6D and FIGS. 7A and 7B. No GUS activity was found in the mature pollens or other tissues at any developmental stages observed.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

Also, it must be noted that, as used herein, the singular forms "a", "an" and "the" include plural aspects unless the context already dictates otherwise. Thus, for example, reference to "a nucleotide sequence of interest" includes a single nucleotide sequence as well as two or more nucleotide sequences; "a plant cell" includes a single cell as well as two or more cells; and so forth.

The claims defining the invention are as follows:

1. A method for effecting specific or preferential expression of a nucleotide sequence of interest in a reproduction-associated plant part, the method comprising effecting transcription of the nucleotide sequence of interest in a plant under the transcriptional control of:
   a nucleotide sequence defining a transcriptional control sequence comprising the nucleotide sequence set forth in SEQ ID NO: 3,
   wherein the nucleotide sequence of interest is heterologous with respect to the transcriptional control sequence.

2. The method of claim 1 wherein the reproduction-associated plant part comprises a plant seed.

3. The method of claim 1 wherein the reproduction-associated plant part comprises an anther.

4. The method of claim 1 wherein said plant is a cereal crop plant.

5. A nucleic acid construct comprising:
   (i) a nucleotide sequence defining a transcriptional control sequence comprising the nucleotide sequence set forth in SEQ ID NO: 3; and
   (ii) a nucleotide sequence of interest that is heterologous with respect to the transcriptional control sequence, and is operably connected to the transcriptional control sequence.

6. A cell comprising either the nucleic acid construct of claim 5; or a genomically integrated form of said nucleic acid construct.

7. The cell of claim 6 wherein the cell is a plant cell.

8. The cell of claim 7 wherein the cell is a cereal crop plant cell.

9. A multicellular structure comprising one or more cells of claim 6.

10. The multicellular structure of claim 9 wherein the multicellular structure comprises a plant or a part, organ or tissue thereof.

11. The multicellular structure of claim 10 wherein said plant is a cereal crop plant.

* * * * *